(12) United States Patent
Safai et al.

(10) Patent No.: US 9,128,030 B1
(45) Date of Patent: Sep. 8, 2015

(54) X-RAY BACKSCATTERING BATTERY INSPECTION

(71) Applicant: The Boeing Company, Chicago, IL (US)

(72) Inventors: Morteza Safai, Newcastle, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 80 days.

(21) Appl. No.: 13/918,565

(22) Filed: Jun. 14, 2013

Related U.S. Application Data

(60) Provisional application No. 61/773,742, filed on Mar. 6, 2013.

(51) Int. Cl.
*G01N 23/00* (2006.01)
*G01N 23/203* (2006.01)

(52) U.S. Cl.
CPC .................. *G01N 23/203* (2013.01)

(58) Field of Classification Search
CPC ........................ G01V 5/0025; G01N 23/203
USPC ................................................ 378/57, 86–90
See application file for complete search history.

(56) References Cited

U.S. PATENT DOCUMENTS

2011/0096901 A1* 4/2011 Kotowski et al. ............... 378/57
2012/0045127 A1   2/2012 Song et al.

FOREIGN PATENT DOCUMENTS

WO        2006056133 A1    6/2006

* cited by examiner

*Primary Examiner* — Hoon Song
(74) *Attorney, Agent, or Firm* — Kunzler Law Group, PC

(57) ABSTRACT

A system may be provided for inspecting a first internal characteristic of a sealed article such as a lithium-ion battery. The system may include an X-ray source, one or more X-ray detectors, one or more actuators that control the location on the article at which the X-rays are emitted, and a processing apparatus that receives X-ray detection data from the one or more X-ray detectors. The processing apparatus may use the X-ray detection data to form an X-ray backscattering image that shows the first internal characteristic. The first internal characteristic may be an electrolyte level within the lithium-ion battery or a material consistency within the lithium-ion battery.

22 Claims, 5 Drawing Sheets

X-RAY BACKSCATTERING BATTERY INSPECTION

CROSS-REFERENCE TO RELATED APPLICATION

This patent application claims the benefit of U.S. Provisional Patent Application No. 61/773,742, filed Mar. 6, 2013, which is incorporated herein by reference.

FIELD

This disclosure relates to systems and methods for inspecting the internal characteristics of an enclosed article, and more particularly, to the use of X-ray backscattering techniques to determine whether the internal components of an article are sound by creating an X-ray backscattering image of the article.

BACKGROUND

Many articles exist that maintain a generally airtight or hermetic seal, or at least remain in an enclosure, in order to function properly. It may be desirable to test the internal characteristics of such an article, such as material consistency, fluid levels, and the like, to determine whether the article is to be replaced and/or repaired. According to conventional methods, the article may be subjected to more invasive tests.

Such methods may run the risk of rendering the article unfit for its intended purpose. Further, such methods may be expensive and/or difficult to carry out. It may be desirable to engage in periodic examination of the internal characteristics of the article, but repeated performance of such testing may multiply the expense and/or inconvenience.

One type of article for which examination of internal characteristics may be desired is a battery, or more specifically, a lithium-ion battery. Lithium-ion batteries may generally maintain a hermetic seal in order to operate properly. Additionally, the batteries may contain electrolytes and other materials that can degrade under the stresses of operation, particularly in the context of aviation. Such stresses may include ambient pressure cycles if the batteries are positioned in an unpressurized part of the aircraft. Additionally, such stresses may include dramatic temperature cycles and/or duty cycles as the aircraft's electrical components are activated and deactivated. Such batteries may be important for the operation of the aircraft's electrical systems.

Accordingly, it is desirable to regularly check the internal characteristics of such batteries. It is further desirable for the testing method used to be non-destructive so that batteries that have passed the test may be readily re-used. Further, it is desirable for the testing method to be rapidly and inexpensively carried out. Yet further, it is desirable for the testing method to be reliable and accurate so that faulty batteries can be easily detected and repaired and/or replaced

SUMMARY

The subject matter of the present application has been developed in response to the present state of the art, and in particular, in response to the problem of, and the desire to test articles, such as aircraft batteries, for seal integrity. Accordingly, the subject matter of the present application has been developed to provide an apparatus, system, and method for optically testing the seal integrity of an article, that overcome at least some of the above-discussed shortcomings of prior art techniques.

According to one embodiment, a system may include an X-ray source positioned to emit X-rays to a first location on an article of which at least a first internal characteristic is to be inspected. The system may also include a first actuator coupled to at least one of the X-ray emitting apparatus and the article to cause the X-ray emitting apparatus to emit X-rays to a second location on the article. The system may further include a first X-ray detector positioned to detect backscattering of the X-rays from the first location and the second location, and a processing apparatus connected to receive X-ray detection data from the first X-ray detector. The processing apparatus may use the X-ray detection data to form an X-ray backscattering image indicting X-rays backscattered from the first location and the second location. The X-ray backscattering image may show the first internal characteristic.

The article may be a lithium-ion battery. The first internal characteristic may be selected from the group consisting of an electrolyte level within the lithium-ion battery, and a material consistency within the lithium-ion battery.

The system may further include a second actuator coupled to at least one of the X-ray emitting apparatus and the lithium-ion battery to cause the X-ray emitting apparatus to emit X-rays to a plurality of additional locations on the lithium-ion battery. The first location, the second location, and the plurality of additional locations may cooperate to define a grid covering at least a portion of a surface of the lithium-ion battery that faces the X-ray source.

The first actuator may be a shield positioned at least partially between the X-ray source and the lithium-ion battery. The shield may have a first aperture, and may be movable along an aperture motion direction relative to the X-ray source to position the first aperture at a first position in which X-rays emitted by the X-ray source pass through the first aperture along a first vector, and a second position in which the X-rays emitted by the X-ray source pass through the aperture along a second vector.

The second actuator may urge relative motion between the lithium-ion battery and the X-ray source along an actuation direction. The actuation direction may be substantially perpendicular to the aperture motion direction.

The system may further have a second X-ray detector positioned to detect backscattering of the X-rays from the first location and the second location. The X-ray source may be positioned generally between the first detector and the second detector. The processing apparatus may be a computing system programmed to analyze the X-ray backscattering image and, based on results of analyzing the X-ray backscattering image, indicate to a user at least one of the electrolyte level, and the material consistency. The X-ray backscattering image may further show a second internal characteristic that is the other of the group consisting of the electrolyte level within the lithium-ion battery, and the material consistency within the lithium-ion battery.

According to one embodiment, a method may include positioning an X-ray source proximate an article of which at least a first internal characteristic is to be inspected, positioning a first X-ray detector proximate the article, emitting X-rays from the X-ray source to a first location on the article, detecting backscattering of the X-rays from the first location with the first X-ray detector, receiving X-ray detection data from the first X-ray detector in a processing apparatus, and using the X-ray detection data to form an X-ray backscattering image indicting X-rays backscattered from the first location and the second location. The X-ray backscattering image may show the first internal characteristic.

The article may be a lithium-ion battery. The first internal characteristic may be selected from the group consisting of an electrolyte level within the lithium-ion battery, and a material consistency within the lithium-ion battery.

The method may further include, after emitting the X-rays from the X-ray source to the first location, using a first actuator to cause the X-ray emitting apparatus to emit X-rays to a second location on the lithium-ion battery. The first actuator may be coupled to at least one of the X-ray emitting apparatus and the lithium-ion battery.

The method may further include using a second actuator coupled to at least one of the X-ray emitting apparatus and the lithium-ion battery to cause the X-ray emitting apparatus to emit X-rays to a plurality of additional locations on the lithium-ion battery. The first location, the second location, and the plurality of additional locations may cooperate to define a grid covering at least a portion of a surface of the lithium-ion battery that faces the X-ray source.

The actuator may be a shield positioned at least partially between the X-ray source and the lithium-ion battery. The shield may have a first aperture. Using the first actuator to cause the X-ray emitting apparatus to emit X-rays to the second location on the lithium-ion battery may include moving the shield along an aperture motion direction relative to the X-ray source to position the first aperture at a second position in which the X-rays emitted by the X-ray source pass through the aperture along a second vector oriented toward the second location. Using the second actuator to cause the X-ray emitting apparatus to emit X-rays to a plurality of additional locations may include urging relative motion between the lithium-ion battery and the X-ray source along an actuation direction substantially perpendicular to the aperture motion direction.

The method may further include detecting backscattering of the X-rays from the first location and the second location with a second detector. The X-ray source may be positioned generally between the first detector and the second detector.

The processing apparatus may be a computing system. The method may further include analyzing the X-ray backscattering image with the computing system, and, based on results of analyzing the X-ray backscattering image, indicating to a user at least one of the electrolyte level, and the material consistency. The X-ray backscattering image may further show a second internal characteristic that is the other of the group consisting of the electrolyte level within the lithium-ion battery, and the material consistency within the lithium-ion battery.

A system according to one embodiment may include an X-ray source positioned to emit X-rays along a first vector to a first location on a lithium-ion battery of which at least a first internal characteristic is to be inspected. The system may further include a first actuator coupled to at least one of the X-ray emitting apparatus and the lithium-ion battery and a second actuator coupled to at least one of the X-ray emitting apparatus and the lithium-ion battery. The second actuator may cooperate with the first actuator to cause the X-ray source to emit X-rays to a plurality of locations on the lithium-ion battery. The plurality of locations may define a grid covering at least a portion of a surface of the lithium-ion battery that faces the X-ray source. The system may further include a first X-ray detector and a second X-ray detector. The first and second X-ray detectors may cooperate to detect backscattering of the X-rays from the plurality of locations. The system may further include a processing apparatus connected to receive X-ray detection data from the first and second X-ray detectors. The processing apparatus may use the X-ray detection data to form an X-ray backscattering image indicating X-rays backscattered from the plurality of locations. The X-ray backscattering image may show the first internal characteristic. The first internal characteristic may be selected from the group consisting of an electrolyte level within the lithium-ion battery, and a material consistency within the lithium-ion battery.

The first actuator may be a shield positioned at least partially between the X-ray source and the lithium-ion battery. The shield may have a first aperture, and may be movable along an aperture motion direction relative to the X-ray source to determine a vector at which X-rays emitted by the X-ray source pass through the first aperture. The second actuator may urge relative motion between the lithium-ion battery and the X-ray source along an actuation direction substantially perpendicular to the aperture motion direction.

The processing apparatus may be a computing system programmed to analyze the X-ray backscattering image and, based on results of analyzing the X-ray backscattering image, indicate to a user at least one of the electrolyte level, and the material consistency. The X-ray backscattering image may further show a second internal characteristic that is the other of the group consisting of the electrolyte level within the lithium-ion battery, and the material consistency within the lithium-ion battery.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
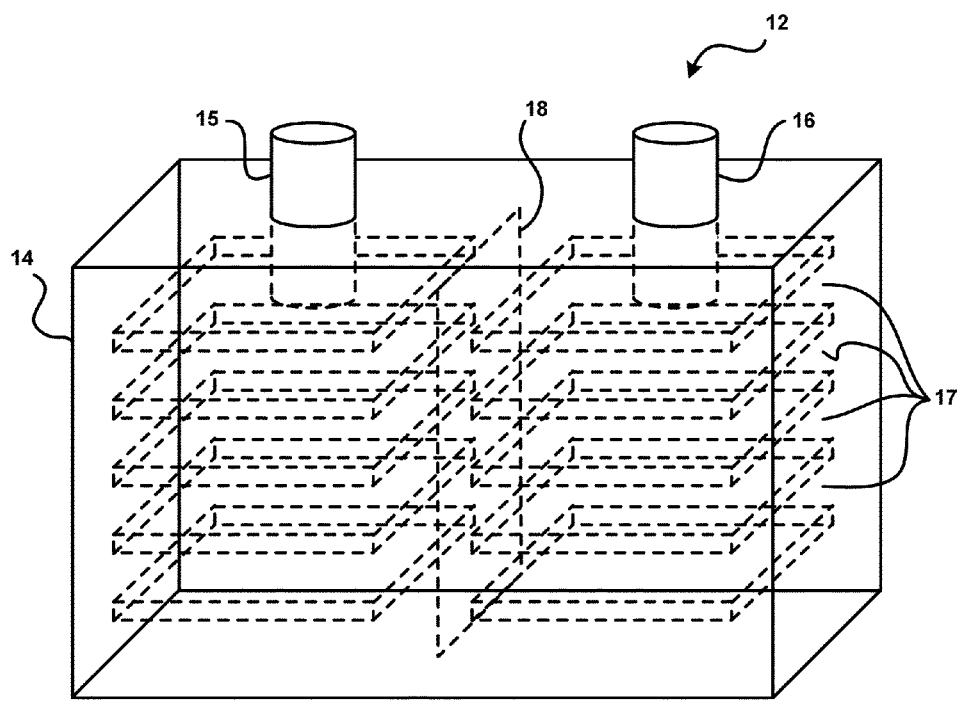
FIG. 1 is a perspective view that illustrates an article in the form of a lithium-ion battery.

Referring to FIG. 1, a perspective view illustrates an article 12 in the form of a generalized lithium-ion battery, the internal characteristics of which may beneficially be tested. The lithium-ion batteries may be of a type commonly used in vehicles such as airplanes (not shown).

The article 12 may have an enclosure that encapsulates and protects its components. The enclosure may take the form of a housing 14 that generally maintains a hermetic seal relative to the environment surrounding the article 12. The housing 14 may contain an anode 15 and a cathode 16, each of which may be formed of parallel plates of a conductive material. The anode 15 and the cathode 16 may be exposed to an electrolyte 17 and a lithium material that cooperate to promote the transport of lithium ions across a separator 18 from the anode 15 to the cathode 16. The result of such transport may be the generation of a potential across the anode 15 and the cathode 16, which may be applied to a load (not shown) such as vehicle circuitry, or more specifically, aircraft circuitry.

Various characteristics of the article 12 may be assessed to help determine that the article 12 is functioning properly. For example, the anode 15, cathode 16, and/or electrolyte 17 may be isolated from ambient moisture and/or air in order to function properly. Thus, the hermetic seal of the housing 14 may be important to the proper functioning of the article 12. Additionally, the level of the electrolyte 17 within the housing 14 and the consistency of the lithium material may also be important factors in the operation of the article 12. All of these characteristics of the article 12 may beneficially be tested on a regular basis to ensure that the article 12 is functioning properly.

Figure 2:
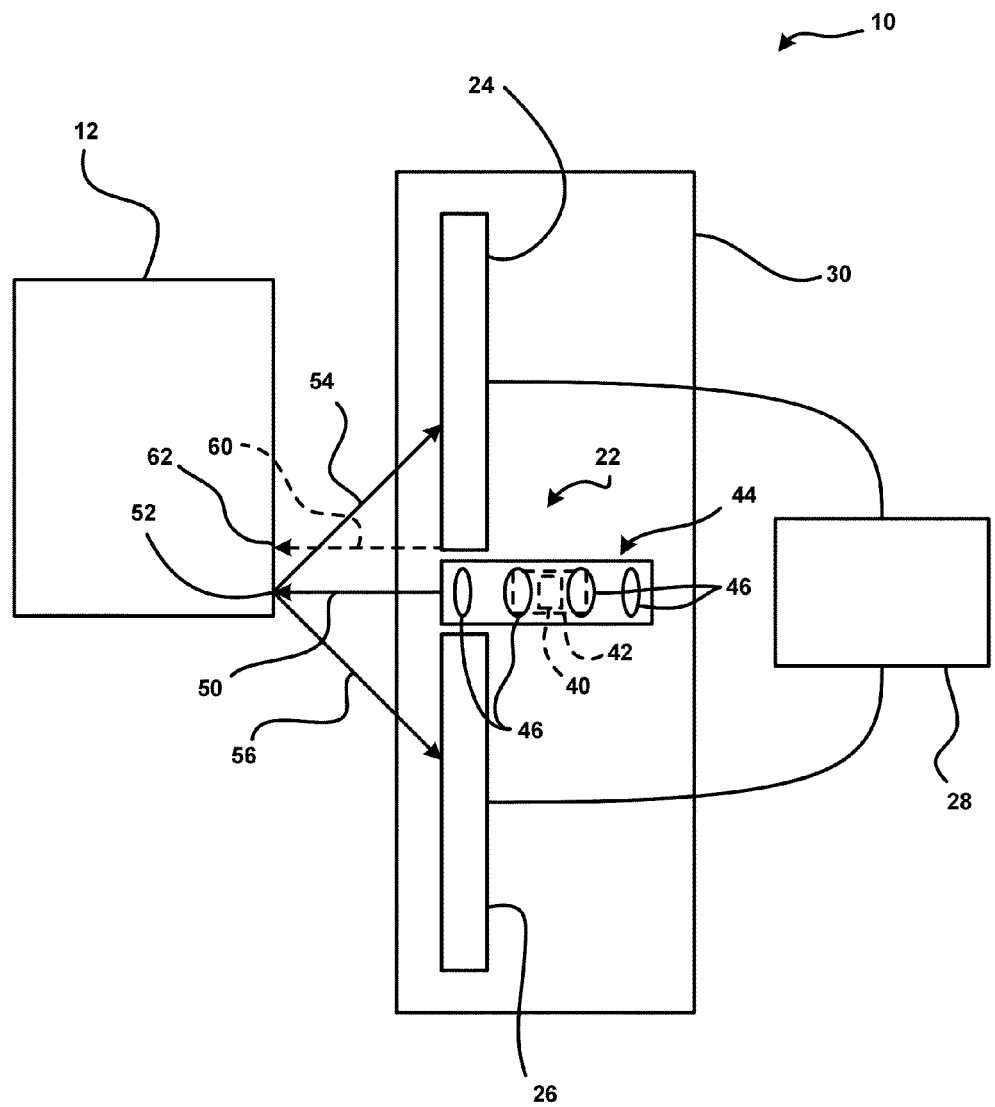
FIG. 2 is a schematic view that illustrates a system for inspecting the internal characteristics of an article, according to one embodiment.

Referring to FIG. 2, a schematic view illustrates a system 10 for inspecting the internal characteristics of an article 12 such as the lithium-ion battery shown in FIG. 1. The system may include an X-ray emitting apparatus 22, a first detector 24, a second detector 26, a processing apparatus 28, and an actuator 30.

In general terms, the X-ray emitting apparatus 22 may emit a focused beam of X-rays toward the article 12. The X-rays may either pass through the article 12 or reflect back (e.g., backscatter) from it, depending on the X-ray opacity of the location on the article 12 where the beam is directed. The reflected or backscattered X-rays may be detected by the first detector 24 and the second detector 26. The X-ray emitting apparatus 22 and the actuator 30 may cooperate to direct the focused beam of X-rays toward a plurality of locations on the surface of the article 12 facing the X-ray emitting apparatus 22 until the entire area of interest has been covered. The resulting X-ray backscattering data may be transmitted from the first detector 24 and the second detector 26 to the processing apparatus 28, which may then create and/or analyze an X-ray backscattering image of the article 12.

The system 10 may operate in a manner distinctly different from conventional X-ray devices, which typically position the item to be inspected between the X-ray source and the detector. A relatively broad X-ray beam is often used, and may image the entire item simultaneously. Such devices may be unable to readily detect certain features such as fluids or internal material inconsistencies, particularly where such inconsistencies are present in a highly X-ray opaque structure. Conversely, the X-ray backscattering techniques described herein may focus on a very narrow portion of an object at a time. Since reflected X-rays (i.e., backscattered X-rays) are measured, rather than penetrating X-rays, additional features of the object may be visible such as fluids and internal material inconsistencies.

Returning to the system 10 of FIG. 2, the X-ray emitting apparatus 22 may include a variety of components including an X-ray source 40, a stationary shield 42, and a movable shield 44. The X-ray source 40 may emit X-rays along a relatively broad swath. The stationary shield 42 may reflect and/or absorb the X-rays except for those that are emitted toward the article 12. The movable shield 44 may have a plurality of apertures 46.

The movable shield 44 may further reflect and/or absorb the remaining X-rays except for those that pass through the aperture 46 that is aligned with the open portion of the stationary shield 42. The open portion of the stationary shield 42 may be sized such that X-rays are only able to pass through one of the apertures 46 at a time. The apertures 46 illustrated in FIG. 2 may be exaggerated in size; the apertures 46 of the movable shield 44 may in reality be very small so as to permit the X-rays to exit the X-ray emitting apparatus 22 only in a focused beam through the aperture 46.

The position of the aperture 46 may determine the vector along which the X-rays exit the X-ray emitting apparatus 22. The movable shield 44 may be designed to rotate so that the aperture 46 that is receiving X-rays is able to move upward or downward, thereby permitting vertical angulation of the exit vector of the X-rays (i.e., motion into or out of the page relative to the top view of FIG. 2). Thus, the movable shield 44 may act as a first actuator that provides for vertical adjustment of the X-ray impingement location on the article 12. The configuration and operation of the X-ray emitting apparatus 22 will be shown and described with greater clarity in connection with FIG. 3.

As shown in FIG. 2, one of the aperture 46 may be aligned with the open portion of the stationary shield 42, and may thus be positioned to emit X-rays toward the article 12 along a first vector 50 to a first location 52 on the surface of the article 12 facing the x-ray emitting apparatus 22. Depending on the X-ray opacity of the material of the article 12 along the first vector 50 (i.e., at the first location 52 and within the article 12 behind the first location 52), some percentage of the X-rays may be reflected back toward the system 10.

The X-rays may reflect along a wide range of angles, but by way of example, a first return vector 54 may reflect from the first location 52 toward the first detector 24 and a second return vector 56 may reflect from the first location 52 toward the second detector 26. The first detector 24 may detect the first return vector 54 and the second detector 26 may detect the second return vector 56. The corresponding X-ray detection data may be transmitted from the first detector 24 and the second detector 26 to the processing apparatus 28.

The system 10 may be designed to produce a two-dimensional image of the article 12. Thus, it may be desirable to adjust the X-ray emitting apparatus 22 to emit X-rays not only vertically, as described above in connection with the movable shield 44 above, but also horizontally. The actuator 30 may accomplish this by providing relative horizontal motion between the X-ray emitting apparatus 22 and the article 12. In the embodiment of FIG. 2, this may be accomplished by moving the X-ray emitting apparatus 22, the first detector 24, and the second detector 26.

In one example, the actuator 30 may include a mobile platform to which the X-ray emitting apparatus 22, the first detector 24, and the second detector 26 are all mounted. For example, the actuator 30 may include a wheeled platform that rolls along a surface or along tracks. In the alternative, the actuator 30 may include a stationary conveyer such as a conveyer belt or linear actuator that provides the desired horizontal relative motion. In any case, the movable shield 44 may operate as a first actuator that controls the vertical orientation of the exit vector of the X-rays from the X-ray emitting apparatus 22, and the actuator 30 may serve as a second actuator that controls the horizontal origin, and therefore destination, of the exit vector. In such an embodiment, the actuation direction of the actuator 30 is horizontal.

Figure 3:
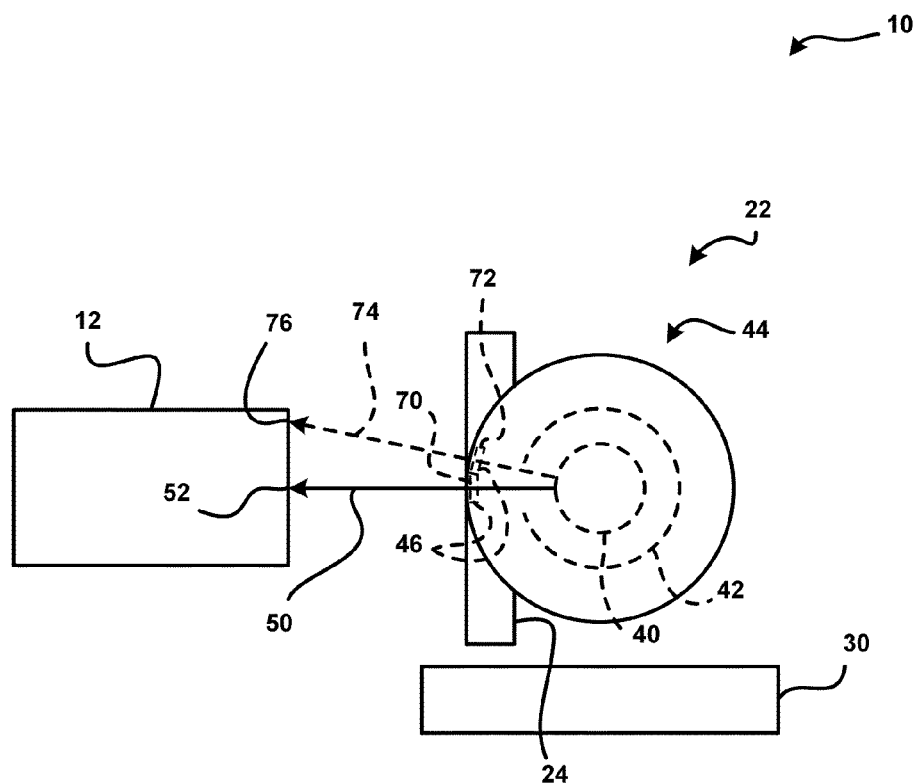
FIG. 3 is a side elevation view of the system of FIG. 2, illustrating emission of X-rays at a second location on the article.

As a result, the movable shield 44 may be actuated (e.g., rotated) to move the aperture 46 through which the X-ray emitting apparatus 22 emits the X-rays, thereby emitting X-rays toward the article 12 along a second vector 74 (shown in FIG. 3). The actuator 30 may operate to move the X-ray emitting apparatus 22, the first detector 24, and the second detector 26 horizontally so that the X-ray emitting apparatus 22 emits the X-rays toward the article 12 along a third vector 60 to a third location 62 on the surface of the article 12 facing the X-ray emitting apparatus 22.

Referring to FIG. 3, a side elevation view of the system of FIG. 2, illustrates the system 10 with the second return vector 56 and the processing apparatus 28 absent to enhance the clarity of the remaining components. FIG. 3 illustrates the emission of X-rays at a second location 76 on the article via the second vector 74. The manner in which this is accomplished via the movable shield 44 may also be more clearly shown.

More particularly, the stationary shield 42 may have the C-shape shown, or any other shape that absorbs or reflects X-rays from the X-ray source 40 except for those that are emitted toward the article 12. X-rays may exit the interior of the stationary shield 42 through the open portion of the C-shape. The apertures 46 may be spaced along the circumference of the movable shield 44 so that only one aperture 46 is aligned with the open portion of the C-shape of the stationary shield 42 at a time. Thus, when the first detector 24 or the second detector 26 detects a backscattered X-ray, it will be from a single known location on the surface of the article 12 that faces the X-ray emitting apparatus 22.

As shown, the aperture 46 aligned with the open portion of the C-shape of the stationary shield 42 may be at a first position 70 that permits X-rays to exit the X-ray emitting apparatus 22 along the first vector 50. The movable shield 44 may then be rotated so that the aperture 46 moves along an aperture motion direction (i.e., upward) to the second position 72 shown in FIG. 3. In the second position 72, X-rays may exit the X-ray emitting apparatus 22 through the aperture 46 along the second vector 74 to impinge against the second location 76 on the article 12.

The movable shield 44 may rotate continuously along a single direction if desired. Thus, the open portion of the C-shape of the stationary shield 42 may be sized relatively precisely so that as the aperture 46 passes upward out of alignment with the open portion of the C-shape, a second aperture 46 of the apertures 46 passes upward, into alignment with the open portion of the C-shape. This may cause X-rays to be emitted along a vertical line on the article 12. Simultaneously, the actuator 30 may cause the X-ray emitting apparatus 22, the first detector 24, and the second detector 26 to move relative to the article 12 at constant speed. In this manner, the surface of the article 12 facing the X-ray emitting apparatus 22 may receive relatively even exposure to the X-rays from the X-ray emitting apparatus 22.

In combination with this motion of the movable shield 44 and the actuator 30, the processing apparatus 28 may receive data from the first detector 24 and the second detector 26 at a relatively constant time interval. As a result, the processing apparatus 28 may receive data from each point in a grid that generally covers the surface of the article 12 that faces the X-ray emitting apparatus 22, or at least the portion of the surface that is of interest for inspection purposes. The locations on the grid where X-ray backscattering data is received and recorded (including the first location 52, the second location 76, the third location 62, and a plurality of additional locations) may be relatively evenly spaced apart. Known techniques such as rasterizing may be used to combine this data into an X-ray backscattering image of the article 12.

The movable shield 44 and the actuator 30 motion described above are merely exemplary. Those of skill in the art will recognize that a wide variety of different actuations may be carried to direct a focused X-ray beam at each point of a grid on an object. According to one alternative embodiment (not shown), a movable shield like the movable shield 44 may have only a single aperture 46, which may move only along an arc that directs the X-rays only to the portion of the article 12 to be inspected. This may allow the non-use of a stationary shield like the stationary shield 42.

According to another alternative embodiment (not shown), an X-ray emitting apparatus may emit X-rays along only a single vector, but the X-ray emitting apparatus may be movable via a separate actuator, such as a vertical linear actuator. Thus, the X-ray emitting apparatus may emit X-rays along a constant, horizontal vector, the origin of which moves horizontally and vertically along the desired grid pattern to direct the X-rays to cover a corresponding grid pattern on the article under inspection.

According to another alternative embodiment (not shown), an X-ray emitting apparatus may be stationary and may emit X-rays only along a single vector. The X-ray emitting apparatus may be coupled to two angular actuators (one with vertical angulation and the other with horizontal angulation) to tilt the X-ray emitting apparatus up and down, and from side to side, to direct the X-rays in the desired grid pattern.

According to still another alternative embodiment, an X-ray emitting apparatus may be stationary, but may have two actuators that control the angle at which X-rays escape the X-ray emitter. For example, in place of the movable shield 44, which may have a generally cylindrical shape, such an X-ray emitting apparatus may have a spherical shield with a single aperture that can pivot horizontally or vertically to direct the X-rays emitted along the desired vector.

Alternatively, a shield for such an X-ray emitting apparatus may have overlapping plates with slots, one vertical and one horizontal. The plate with the horizontal slot may move vertically to control the vertical angulation of the emitted X-rays, while the plate with the vertical slot may move horizontally to control the horizontal angulation of the emitted X-rays.

Many modifications of the first detector 24, and the second detector 26 are also possible; they are illustrated as relatively flat plates in FIGS. 2 and 3, but in alternative embodiments, could be rounded or shaped differently. Additionally, two X-ray detectors need not be used; rather, one or more than two X-ray detectors may be used in alternative embodiments.

The processing apparatus 28 may be any type of device capable of receiving and processing image data. The processing apparatus 28 may be a microprocessor-based computer, an ASIC, a terminal connected to a network that provides processing functionality, or any other known type of computing apparatus. The processing apparatus 28 may carry out instructions to receive, record, and process the images via software, hardware, or any other method known in the art. If desired, the processing apparatus 28 may also act as a control system to control the various components of the system 10, including the X-ray emitting apparatus 22, the first detector 24, the second detector 26, and the actuator 30. The processing apparatus 28 may have programming that automates the inspection process.

Those of skill in the art will recognize that the system 10 may be modified in numerous other ways. Many more alternative embodiments may be conceived with the aid of the present disclosure.

Figure 4:
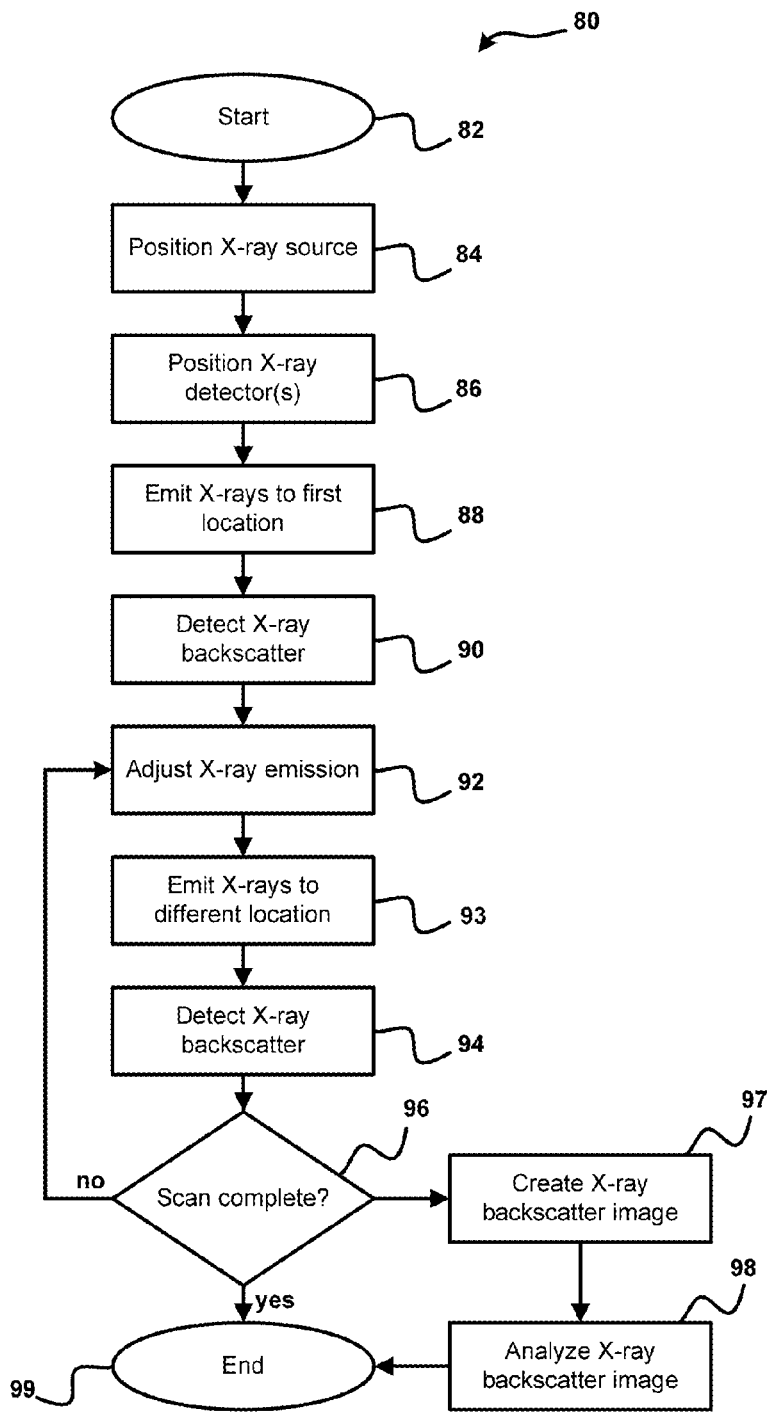
FIG. 4 is a flowchart illustrating a method for inspecting the internal characteristics of an article through the use of a system such as that of FIGS. 2 and 3.

Referring to FIG. 4, a flowchart illustrates a method 80 for non-invasively inspecting the internal characteristics of an article 12 such as a lithium-ion battery through the use of a system such as the system 10 of FIGS. 2 and 3. In alternative embodiments, the method 80 may be carried out through the use of a system (not shown) different from the system 10 of FIGS. 2 and 3. Alternatively, the system 10 of FIGS. 2 and 3 may be used with a method (not shown) different from the method 80. The following description will reference the system 10 of FIGS. 2 and 3 for clarity.

As mentioned above, the processing apparatus 28 may be designed to act as a controller for the system 10, and may thus control the performance of the various steps of the method 80. Alternatively, a different control system may be used, or the method 80 may be manually carried out.

The method 80 may start 82 with a step 84 in which the X-ray emitting apparatus 22 is positioned relative to the article 12 to be inspected. This step 84 may also entail actuating the movable shield 44 and/or the actuator 30 to position the X-ray emitting apparatus 22 to emit X-rays along a starting vector, such as the first vector 50 of FIGS. 2 and 3.

In a step 86, the first detector 24 and the second detector 26 may also be positioned. The first detector 24 and the second detector 26 may be positioned near the article 12 so as to provide a high probability of receiving reflected X-rays such as those travelling along the first return vector 54 and the second return vector 56 in FIG. 2. As also illustrated in FIG. 2, the first detector 24 and the second detector 26 may be positioned on either side of the X-ray emitting apparatus 22.

In a step 88, the X-ray emitting apparatus 22 may emit X-rays to a first location on the article 12, such as the emission of X-rays along the first vector 50 to the first location 52 as shown in FIG. 2. Then, backscatter from the X-rays emitted may be detected by the first detector 24 and/or the second detector 26 in a step 90. This may provide the first data point for an X-ray backscattering image that may ultimately be produced through the use of the method 80.

In a step 92, the X-ray emitting apparatus 22 may be adjusted to emit X-rays at a different location on the article 12, such as the third location 62 or the second location 76 shown in FIGS. 2 and 3. This be done through the use of the actuator(s) that control X-ray impingement on the article 12, for example, the movable shield 44 and the actuator 30. One or both of the movable shield 44 and the actuator 30 may be actuated between detection steps. If desired, the movable shield 44 and the actuator 30 may both move substantially continuously until scanning is complete.

In a step 93, the X-ray emitting apparatus 22 may emit X-rays to the different location on the article 12, such as the emission of X-rays along the third vector 60 to the third location 62 or along the second vector 74 to the second location 76 shown in FIGS. 2 and 3. Then, backscatter from the X-rays emitted may be detected by the first detector 24 and/or the second detector 26 in a step 94. This may provide another point for the X-ray backscattering image.

Then, in a query 96, the method 80 may determine whether scanning of the article 12 is complete. This may entail determining whether the X-rays have been directed at each location (for example, each grid point) on the surface of the article 12 to be inspected.

If scanning is not complete, the step 92, the step 93, and the step 94 may be repeated by adjusting the X-ray emitting apparatus 22, emitting X-rays at the new location on the article 12, and detecting backscatter from the emitted X-rays. Each iteration of the step 92, the step 93, and the step 94 may generate one or more additional data points for the X-ray backscattering image.

Once scanning is complete, the X-ray backscattering image may be created. This may be done by the processing apparatus 28, or through the use of a different data processing system. According to one example, the X-ray backscattering image is created by rasterizing the X-ray backscattering data in the processing apparatus 28 to form the image. This may be done, for example, by assigning a value to each pixel or region of an image based on the intensity of X-ray backscattering detected at the corresponding location on the article 12.

Once the X-ray backscattering image has been obtained, the X-ray backscattering image may be analyzed to form conclusions regarding the internal characteristic(s) of the article 12 that are to be inspected. Inspection may be done manually, for example, by an operator of the system 10 who receives the X-ray backscattering image, looks for certain features that are or are not desired, and records an evaluation of the internal characteristic(s) of the article 12. Alternatively, the inspection may be done automatically, for example, through the use of a computing system. According to one embodiment, automated inspection may be done by the processing apparatus 28.

Figure 5:
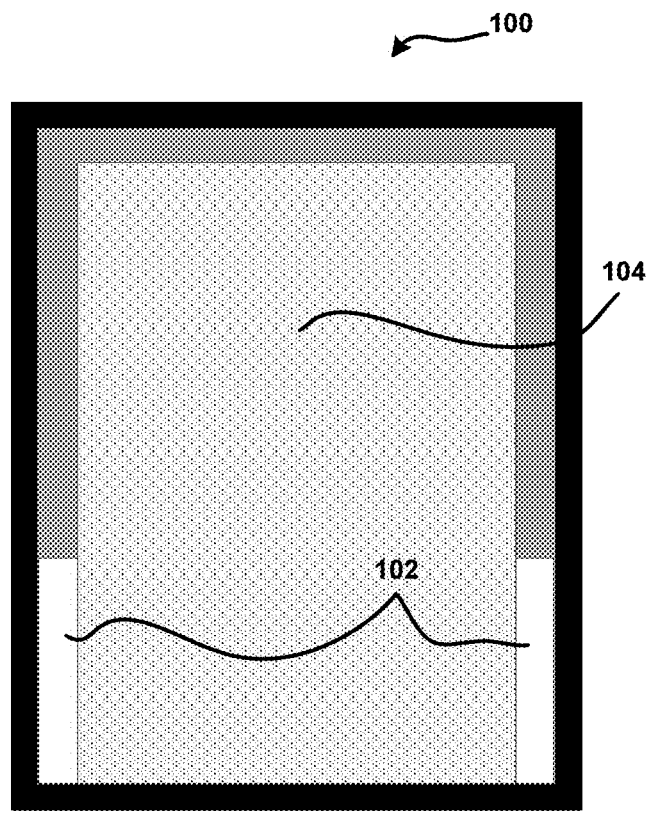
FIG. 5 is a representation of an X-ray backscattering image that, by way of example, may be produced with the system of FIGS. 2 and 3.

Referring to FIG. 5, a representation of an X-ray backscattering image 100 is shown that, by way of example, may be produced with the system 10 of FIGS. 2 and 3 and/or the method 80 of FIG. 3. The X-ray backscattering image 100 has dark areas and light areas. The article 12 may have a housing (e.g., the housing 14 of the lithium-ion battery of FIG. 1) that has a relatively uniform thickness and material consistency, and hence, a relatively uniform X-ray opacity. Thus, the light areas may represent internal features that are generally more X-ray opaque. Light areas may indicate the presence of fluids, materials of relatively high density and/or X-ray opacity, or the like.

Many different internal characteristics may be inspected. Two of these are particularly pertinent to batteries, and more particularly to lithium-ion batteries. One of these key internal characteristics may be the level of electrolyte within the battery. The electrolyte may be in liquid form, and may thus be difficult or impossible to view with conventional X-ray technology. A level of electrolyte that is too high or too low may indicate that the battery is no longer fully functional. A second key internal characteristic for batteries may be the consistency of a material within the battery, such as a lithium material.

Both of these characteristics may be observed by analyzing an X-ray backscattering image like the X-ray backscattering image 100 of FIG. 5. For example, an electrolyte level 102 of the battery may be determined by measuring the relatively bright patches at the sides of the image. The top surface of the electrolyte may be clearly visible as the relatively bright patch transitions to a relatively dark area.

As another example, a material 104 within the battery may also be observed. If the central region of the X-ray backscattering image 100 has anomalies such as unexplained voids (dark patches), unexplained aggregations of X-ray opaque material (bright patches), or the like, it may indicate that the material 104 has begun to degrade. Those of skill in the art will recognize that many other internal characteristics of a battery or other article 12 may be inspected via analysis of an X-ray backscattering image such as the X-ray backscattering image 100. If desired, the article to be inspected may have a serial number or other marking designed to be visible in the X-ray backscattering image to allow easy reference and recording of the results of the inspection.

Many different methods may be used to perform the step 98 of analyzing an X-ray backscattering image such as the X-ray backscattering image 100. Visual analysis may be performed by a user to examine the features shown such the electrolyte level 102 and the material 104. Alternatively, computer-implemented methods may be used to automatically perform the analysis, for example, in the processing apparatus 28, with similar techniques or other techniques known in the art of digital image analysis.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A system comprising:
an X-ray source positioned to emit X-rays to a first location on an article of which at least a first internal characteristic is to be inspected;
a first actuator coupled to at least one of the X-ray source and the article to cause the X-ray source to emit X-rays to a second location on the article;
a first X-ray detector positioned to detect backscattering of the X-rays from the first location and the second location; and
a processing apparatus connected to receive X-ray detection data from the first X-ray detector, wherein the processing apparatus uses the X-ray detection data to form an X-ray backscattering image indicating X-rays backscattered from the first location and the second location;
wherein the X-ray backscattering image shows the first internal characteristic;
wherein the article comprises a battery; and
wherein the first internal characteristic is selected from a group consisting of an electrolyte level within the battery and a material consistency within the battery.

2. The system of claim 1, further comprising a second actuator coupled to at least one of the X-ray source and the battery to cause the X-ray source to emit X-rays to a plurality of additional locations on the battery such that the first location, the second location, and the plurality of additional locations cooperate to define a grid covering at least a portion of a surface of the battery that faces the X-ray source.

3. The system of claim 2, wherein the first actuator comprises a shield positioned at least partially between the X-ray source and the battery, the shield comprising a first aperture, wherein the shield is movable along an aperture motion direction relative to the X-ray source to position the first aperture at a first position in which X-rays emitted by the X-ray source pass through the first aperture along a first vector, and a second position in which the X-rays emitted by the X-ray source pass through the aperture along a second vector.

4. The system of claim 3, wherein the second actuator urges relative motion between the battery and the X-ray source along an actuation direction substantially perpendicular to the aperture motion direction.

5. The system of claim 1, further comprising a second X-ray detector positioned to detect backscattering of the X-rays from the first location and the second location, wherein the X-ray source is positioned generally between the first detector and the second detector.

6. The system of claim 1, wherein the processing apparatus comprises a computing system programmed to analyze the X-ray backscattering image and, based on results of analyzing the X-ray backscattering image, indicate to a user at least one of the electrolyte level, and the material consistency.

7. The system of claim 1, wherein the X-ray backscattering image further shows a second internal characteristic comprising another of the group consisting of the electrolyte level within the battery and the material consistency within the battery.

8. A method comprising:
positioning an X-ray source proximate to an article of which at least a first internal characteristic is to be inspected;
positioning a first X-ray detector proximate the article;
emitting X-rays from the X-ray source along to a first location on the article;
detecting backscattering of the X-rays from the first location with the first X-ray detector;
receiving X-ray detection data from the first X-ray detector in a processing apparatus; and
using the X-ray detection data to form an X-ray backscattering image indicating X-rays backscattered from the first location;
wherein the X-ray backscattering image shows the first internal characteristic;
wherein the article comprises a battery; and
wherein the first internal characteristic is selected from a group consisting of an electrolyte level within the battery and a material consistency within the battery.

9. The method of claim 8, wherein the battery is a lithium-ion battery.

10. The method of claim 8, further comprising, after emitting the X-rays from the X-ray source to the first location, using a first actuator coupled to at least one of the X-ray source and the battery to cause the X-ray source to emit X-rays to a second location on the battery.

11. The method of claim 10, further comprising using a second actuator coupled to at least one of the X-ray source and the battery to cause the X-ray source to emit X-rays to a plurality of additional locations on the battery such that the first location, the second location, and the plurality of additional locations cooperate to define a grid covering at least a portion of a surface of the battery that faces the X-ray source.

12. The method of claim 11, wherein the first actuator comprises a shield positioned at least partially between the X-ray source and the battery, the shield comprising a first aperture, wherein using the first actuator to cause the X-ray source to emit X-rays to the second location on the battery comprises moving the shield along an aperture motion direction relative to the X-ray source to position the first aperture at a second position in which the X-rays emitted by the X-ray source pass through the aperture along a vector oriented toward the second location.

13. The method of claim 12, wherein using the second actuator to cause the X-ray source to emit X-rays to a plurality of additional locations comprises urging relative motion between the battery and the X-ray source along an actuation direction substantially perpendicular to the aperture motion direction.

14. The method of claim 8, further comprising detecting backscattering of the X-rays from the first location with a second detector, wherein the X-ray source is positioned generally between the first detector and the second detector.

15. The method of claim 8, wherein the processing apparatus comprises a computing system, the method further comprising:
analyzing the X-ray backscattering image with the computing system; and
based on results of analyzing the X-ray backscattering image, indicating to a user at least one of the electrolyte level, and the material consistency.

16. The method of claim 9, wherein the X-ray backscattering image further shows a second internal characteristic comprising another of the group consisting of the electrolyte level within the battery and the material consistency within the battery.

17. A system comprising:
an X-ray source positioned to emit X-rays along a first vector to a first location on a battery of which at least a first internal characteristic is to be inspected;
a first actuator coupled to at least one of the X-ray source and the battery;
a second actuator coupled to at least one of the X-ray source and the battery, wherein the second actuator cooperates with the first actuator to cause the X-ray source to emit X-rays to a plurality of locations on the battery, the plurality of locations defining a grid covering at least a portion of a surface of the battery that faces the X-ray source;
a first X-ray detector;
a second X-ray detector, wherein the first and second X-ray detectors cooperate to detect backscattering of the X-rays from the plurality of locations; and
a processing apparatus connected to receive X-ray detection data from the first and second X-ray detectors, wherein the processing apparatus uses the X-ray detection data to form an X-ray backscattering image indicating X-rays backscattered from the plurality of locations;
wherein the X-ray backscattering image shows the first internal characteristic;
wherein the first internal characteristic is selected from a group consisting of an electrolyte level within the battery and a material consistency within the battery.

18. The system of claim 17, wherein the first actuator comprises a shield positioned at least partially between the X-ray source and the battery, the shield comprising a first aperture, wherein the shield is movable along an aperture motion direction relative to the X-ray source to determine a vector at which X-rays emitted by the X-ray source pass through the first aperture, wherein the second actuator urges relative motion between the battery and the X-ray source along an actuation direction substantially perpendicular to the aperture motion direction.

19. The system of claim 18, wherein the processing apparatus comprises a computing system programmed to analyze the X-ray backscattering image and, based on results of analyzing the X-ray backscattering image, indicate to a user at least one of the electrolyte level, and the material consistency, wherein the X-ray backscattering image further shows a second internal characteristic comprising another of the group consisting of the electrolyte level within the battery, and the material consistency within the battery.

20. A system comprising:
an X-ray source positioned to emit X-rays to a first location on an article of which at least a first internal characteristic is to be inspected;
a stationary shield comprising an open portion through which X-rays from the X-ray source pass;
a movable shield coupled to at least one of the X-ray source and the article to cause the X-ray source to emit X-rays to a second location on the article, the movable shield comprising at least one aperture through which X-rays passing through the open portion of the stationary shield pass;

a mobile platform movable relative to the article to cause the X-ray source to emit X-rays to a third location on the article, the X-ray source, stationary shield, and movable shield being mounted to the mobile platform;

a first X-ray detector positioned to detect backscattering of the X-rays from the first location, the second location, and the third location; and a processing apparatus connected to receive X-ray detection data from the first X-ray detector, wherein the processing apparatus uses the X-ray detection data to form an X-ray backscattering image indicating X-rays backscattered from the first location, the second location, and the third location;

wherein the X-ray backscattering image shows the first internal characteristic;

wherein the article comprises a battery; and wherein the first internal characteristic is selected from a group consisting of an electrolyte level within the battery and a material consistency within the battery.

21. The system of claim 20, wherein the movable shield moves in a first direction and the mobile platform moves in a second direction, the first direction being perpendicular to the second direction.

22. The system of claim 1, wherein the battery is a lithium-ion battery.

* * * * *